United States Patent [19]

Mahoney

[11] Patent Number: 4,727,035
[45] Date of Patent: Feb. 23, 1988

[54] IMMUNOASSAY FOR CYCLOSPORIN

[76] Inventor: Walter C. Mahoney, 7628 Dunmore Dr., Woodbury, Minn. 55125

[21] Appl. No.: 671,302

[22] Filed: Nov. 14, 1984

[51] Int. Cl.$^4$ ............... G01N 33/53; G01N 33/533; G01N 33/534; G01N 33/541
[52] U.S. Cl. .................... 436/518; 436/540; 436/542; 436/545; 436/546; 436/804; 436/815
[58] Field of Search ............ 436/518, 545, 546, 815, 436/540, 542, 804

[56] References Cited

U.S. PATENT DOCUMENTS

| 4,108,985 | 8/1978 | Ruegger et al. |
| 4,210,581 | 7/1980 | Ruegger et al. |
| 4,215,199 | 7/1980 | Harri et al. |
| 4,220,641 | 9/1980 | Traber et al. |
| 4,288,431 | 9/1981 | Traber et al. |
| 4,289,851 | 9/1981 | Traber et al. |
| 4,384,996 | 5/1981 | Bollinger et al. |
| 4,388,307 | 6/1983 | Cavanak. |
| 4,396,542 | 8/1983 | Wenger. |

OTHER PUBLICATIONS

Mahoney and Orf, Clin. Chem., 31(3), 459–462, (1985).
Van Vunakis, H. in "Methods in Enzymology", vol. 70, pp. 201–207, Academic Press, N.Y., 1980.
Donatsch, P. et al., J. Immunoassay, 2(1), 19–32, (1981).
"Ciclosporin RIA-Kit, Instructions for Use (Third Edition)", Sandoz Ltd., Basle, Switzerland, (1984).
G. Maner, et al., "3H-OL 27-400: Isolation and Structure Elucidation of Its Metabolites", Sandoz Ltd., Basle, Switzerland, (1981).
W. Mahoney, et al., J. Biol. Chem., 255:11199–11203, (1980).
M. Hermodson, et al., Methods in Enzymology, 91, (Part 1): 352–359, (1983).
J. Pearsen, et al., J. Chromatogr., 207:325–332, (1981).
J. Petcher, et al., Helvetica Clinica Acta, 59:1480–1489, (1976).
D. Taylor, Int'l J. Applied Radiation and Isotopes, 31:192–193, (1980).
Abraham, et al., "Solid Phase Radioimmunoassay of Serum Estradiol-17β: A Semi-Automated Approach", in Immunologic Methods in Steroid Determination, Peron, ed., pp. 87–112, (Meredith Corp., 1970).
Atassi, "Perspectives of the Immunology of Proteins", in Immunology of Proteins, vol. 2, Atassi, ed., pp. 1–25, (Plenum Press, New York, 1977).
Atassi, Mol. Cell. Biochem., 32:21–43, (1980).
Quesniaux, et al., Clin. Chem., 33(1):32–37, (1987).

Primary Examiner—Sidney Marantz
Attorney, Agent, or Firm—Dorsey & Whitney

[57] ABSTRACT

An immunoassay is disclosed which measures the concentration of cyclosporin analytes in sample fluids. Also disclosed is radioiodinated cyclosporin having a specific activity greater than 50 ulCi/ug and fluorescent labeled cyclosporin, both of which is cross-reactive with cyclosporin analytes.

12 Claims, 2 Drawing Figures

IMMUNOASSAY FOR CYCLOSPORIN

BACKGROUND OF THE INVENTION

This invention relates to an immunoassay which measures the concentration of cyclosporin analytes in sample fluids.

Cyclosporins (i.e. cyclosporins A, B, C and D) are 11 amino acid residue cyclic peptides which were discovered during the search for new antifungal compounds. Although initially proposed to be antibiotic, antiarthritic and antiinflammatory compounds, their actions as immunosuppressives have come to outweigh all other uses. This is especially so in the case of cyclosporin A. This compound has had an enormous impact upon the continuation of research on human tissue transplantation leading some to suggest that tissue typing and matching are no longer needed for cyclosporin recipients.

Patients receiving cyclosporin A alone or in conjunction with prednisone therapy, subsequent to tissue transplantation, show a lower incidence of tissue rejection, lower incidence of infection, higher graft survival rates, and greater long-term survival rates, when compared to conventional therapeutic protocols. However, the clinical use of cyclosporin A is complicated by the narrow therapeutic window that exists between the inadequate immunosuppression that occurs at low doses and the adverse effects of hepatotoxicity, nephrotoxicity and sepsis resulting from overadministration.

The only way that cyclosporin A can be efficaciously administered is by periodic monitoring of plasma drug concentrations. For this to be accomplished, an easy assay for determining cyclosporin A levels needs to be developed. An easy assay for cyclosporins B, C and D would also be useful insofar as such compounds find clinical acceptance similar to that of cyclosporin A.

Currently, two types of assays are available for measuring patient drug levels: high-performance liquid chromatography and radioimmunoassay using a 3H-cyclosporin tracer. Both the HPLC assay and the tritiated assay are time consuming for personnel, expensive to perform, and generally too slow in providing data. Thus, there is a need for radioiodine immunoassay and fluorescence immunoassay of cyclosporins.

SUMMARY OF THE INVENTION

The invention involves a method of immunoassay which measures the concentration of cyclosporin analytes in sample fluids. The method includes the basic step of a competitive reaction between labeled cyclosporin and the cyclosporin analyte for an antibody specific to these two compounds. The quantity and specific activity of the labeled cyclosporin and the quantity and reactivity of the antibody are sufficient to give a measurable detection signal representative of the ratio of antibody bound labeled cyclosporin to unbound labeled cyclosporin. Because of the competitive reaction, antibody bound labeled cyclosporin will be inhibited by cyclosporin analyte in the sample.

The competitive reaction may involve simultaneous reaction of the labeled cyclosporin and the cyclosporin analyte with the antibody. For example, the labeled cyclosporin and the antibody may be added to a sample fluid containing an unknown amount of cyclosporin analyte. The competitive reaction of labeled cyclosporin and cyclosporin analyte for antibody would thus be simultaneous.

The competitive reaction may alternatively involve first reacting either the labeled cyclosporin or the cyclosporin analyte, allowing such reaction to substantially reach equilibrium, and second reacting the product of the first reaction with the other of the two compounds.

The basic competitive reaction may be but a part of a more complex assay such as double antibody immunoassay in which a second antibody, specific to the first antibody, causes precipitation upon binding first antibody bound labeled cyclosporin. The basic competitive reaction may be part of a solid phase immunoassay in which, for example, the antibody, specific to labeled cyclosporin, is bound or attached to a solid support. Still other assay types and configurations may be used in conjunction with the basic competitive reaction. All such assays utilizing the basic competitive reaction come within the bounds of the invention.

The labeled cyclosporin may be labeled cyclosporin A, B, C or D. The cyclosporin may be labeled with radioiodine such as $^{125}I$ or $^{131}I$ or with a fluorescent label such as, for example, fluorescein isothiocyanate.

The foregoing immunoassay will measure the concentration of cyclosporin analytes which are cross-reactive with cyclosporin A, B, C or D, depending upon the specificity of the antibody used. Cyclosporin analytes may include cyclosporin A, B, C or D themselves as well as their hydrogenated analogues dihydrocyclosporin A, B, C or D. Cyclosporin analyte may also include fragments or other analogues of cyclosporin. These may include cyclosporin metabolites known as metabolite 1, 8, 10, 13, 17, 18 and 21 (structures and cross-reactivity shown in "Ciclosporin RIA-Kit, Instructions for Use (Third Edition)", Sandoz Ltd., Basle, Switzerland (1984) and G. Maner, et al., "3H-OL 27-400: Isolation and Structure Elucidation of its Metabolites", Sandoz Ltd., Basle, Switzerland (1981), both documents incorporated herein by reference thereto).

The invention also includes the compounds 125I-cyclosporin (either A, B, C or D) having a specific activity greater than 50 uCi/ug and the compounds fluorescein isothiocyanate-cyclosporin (either A, B, C or D). The invention still further includes an immunoassay kit as an article of manufacture. The kit contains labeled cyclosporin (A, B, C or D), the label being radioiodine or a fluorescent label, and an antibody specific to the labeled cyclosporin.

DESCRIPTION OF THE PREFERRED EMBODIMENT

The following describes the labeling of cyclosporin A by $^{125}I$. Cyclosporin A (Sandoz Pharmaceutical) was dissolved in 95% ethanol (percentages herein are vol.-/vol. unless indicated otherwise) at a concentration of 5 mg per ml and stored at −20 degrees C. Two ul (10 ug) of the ethanolic solution was transfered to a 400 ul Eppendorf tube containing 100 ul of 0.1% trifluoroacetic acid (adjusted to pH 2.7 using 1 N sodium hydroxide). Radioiodine (Amersham) (2 mCi) and 100 ul of chloramine T (10 mg per ml) were added, mixed and allowed to stand on ice for 1 minute. Subsequently, 125 ul of a, metabisulphite solution (20 mg per ml) were then added to the reaction mixture.

Iodobeads (Pierce Chemical) can alternatively be used as a replacement for the liquid phase chloramine T. Using a 12×75 mm glass test tube, ethanolic cyclosporin A (10 ug) was added to 100 ul of 0.1% trifluoroacetic acid. This was followed immediately by the addition of radioiodine (3 mCi) and 3 iodobeads. The reaction mixture was then vortexed and allowed to react at room temperature for 20 minutes.

Figure 1:
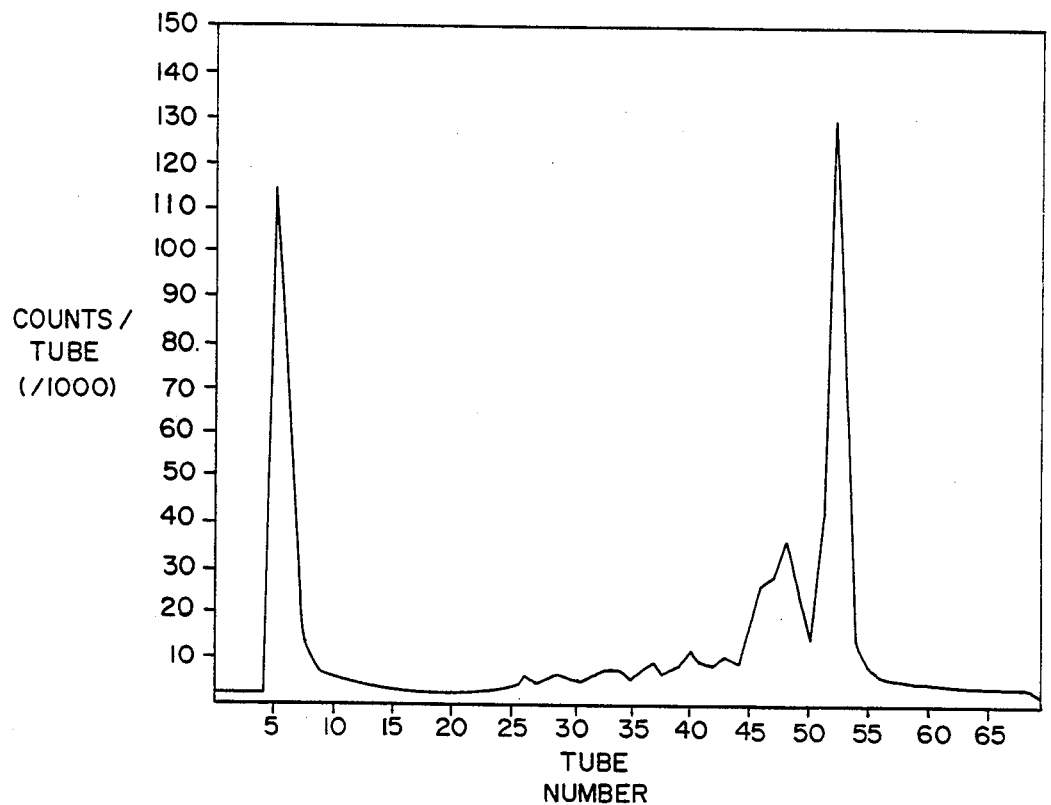
FIG. 1 shows isolation of $^{125}I$-cyclosporin A by high performance liquid chromatography.

The resulting iodinated mixture (from either procedure) was separated using a Varian 5060 high-performance liquid chromatograph equipped with a Model 7125 Rheodyne injector with a 500 ul loop. The sample was applied to a Synchrom (Linden, Ind.) RP-P reversed phase large pore support (0.46×25-cm), which had been equilibrated with redistilled 0.1% trifluoroacetic acid at ambient temperature (according to the methods of W. Mahoney, et al., *J. Biol. Chem.*, 255: 11199–11203 (1980); M. Hermodson, et al., *Methods in Enzymology*, 91 (Part 1): 352–359 (1983); J. Pearson, et al., *J. Chromatogr.*, 207: 325–332 (1981); all references incorporated herein by reference thereto). Successful iodination of cyclosporin A is illustrated in FIG. 1. $^{125}$I-cyclosporin A was isolated by high performance liquid chromatography. Iodocyclosporin was applied to a SynChrom RP-P support (0.45×25 cm) and eluted with a 60 minute linear gradient from 0 to 60% (vol.) acetonitrile in 0.1% trifluoroacetic acid at ambient temperature, 0.8 ml/min. flow rate and 56 atm. pressure. One ml fractions were collected, counted using a gamma counter, and the appropriate samples dried under a stream of purified nitrogen.

The $^{125}$I-cyclosporin elutes at approximately 50 minutes after the start of the acetonitrile gradient. This time is identical to that expected from the elution of nonradioactive iodocyclosporin chromatographed using identical conditions. In contrast to the general belief that high column temperatures (70 degrees C.) are required in order to obtain efficient elution of cyclosporin, the chromatography system used herein provides high resolution and good yields at ambient temperatures. The specific activity has been varied from 5–300 uCi per ug of cyclosporin without any detectable degradation of the compound (as measured by retention time and reaction with antibody).

In general, iodinations can take two forms: either by a substitution reaction or via an oxidation reaction mechanism. Substitution reactions usually occur at neutral pH and result in the iodination of phenolic or imidazole derivatives. Oxidations occur at acid pH and can result in the iodination of indole and sulfur containing compounds. In addition, at low pH halides can be added to unsaturated carbon-carbon bonds. Cyclosporin does not possess any amino acids that can be readily iodinated by substitution methods. However, there is a single amino acid that is singly unsaturated and has been identified as (2S, 3R, 4R, 6E)-3-hydroxy-4-methyl-2 methylamino-6-octenoic acid. This amino acid in cylcosporin A is available to an oxidative iodination approach. This amino acid is also available for iodination on cyclosporins B, C and D.

That this unusual amino acid is the site of iodination is further supported by the determination of the crystal structure of cyclosporin by the addition of iodine to this same amino acid residue. Cf. J. Petcher, et al., *Helvetica Clinica Acta*, 59: 1480–1489 (1976).

Figure 2:
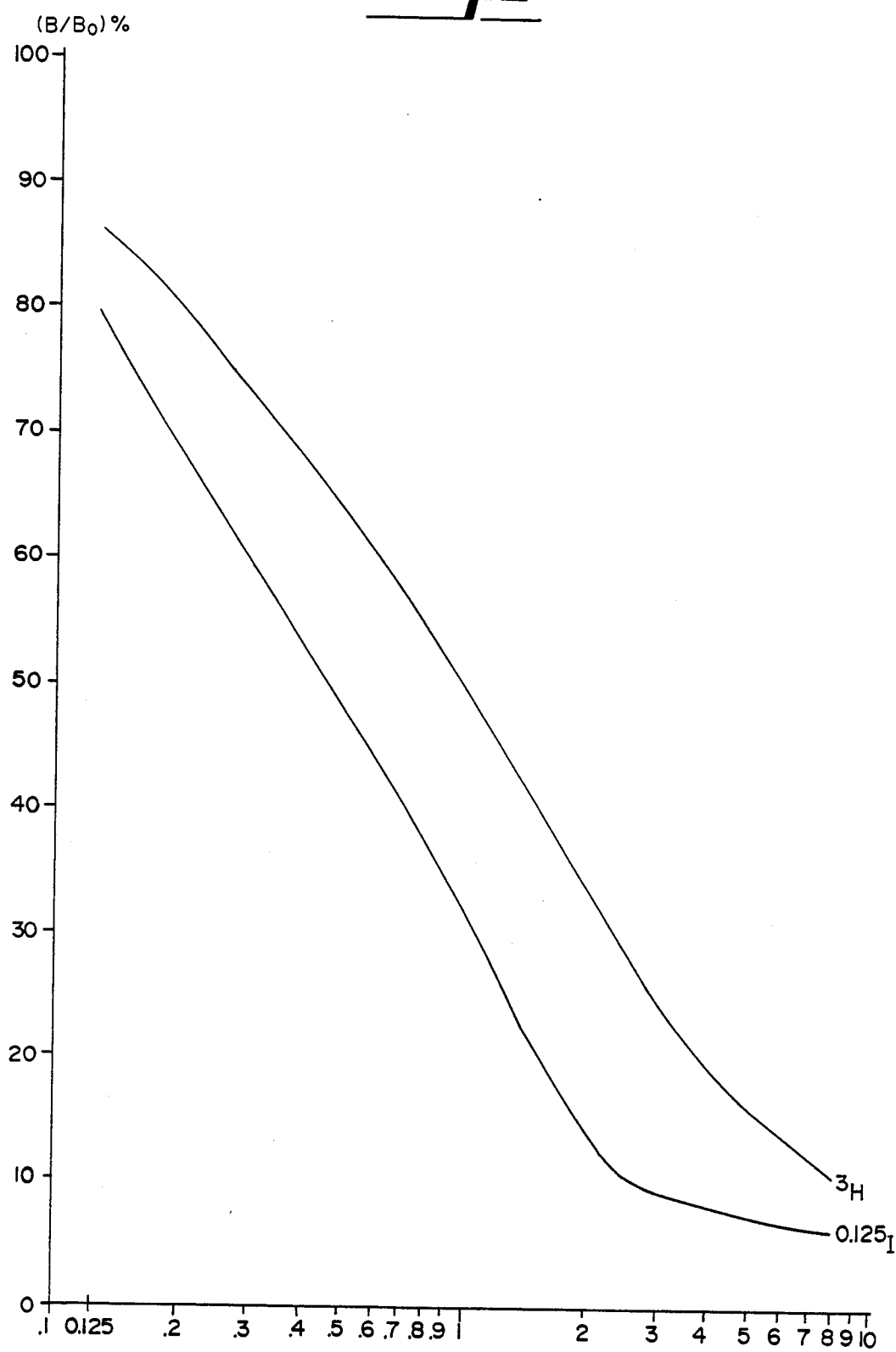
FIG. 2 shows comparison of B/Bo- plots of $^3H$-cyclosporin and $^{125}I$-cyclosporin.

The reaction of $^{125}$I-cyclosporin with antibody generated against cyclosporin C (available commercially from Sandoz Ltd., Basle, Switzerland) is specific and suppressible by the addition of unlabeled cyclosporin A as shown in FIG. 2. Standards were set at 0.125, 0.5, 2.0, 4.0 and 8.0 ng of cyclosporin per 0.1 ml. All other assay steps were as set forth in "Ciclosporin RIA-Kit, Instructions for Use (Third Edition)", Sandoz Ltd., Basle, Switzerland (1984), incorporated herein by reference thereto.

As shown in FIG. 2, the comparison of $^{125}$I-cyclosporin with $^3$H-cyclosporin demonstrates near equivalence (both lines are parallel with almost identical slopes). However, the $^{125}$I-cyclosporin tracer, labeled at 260 uCi per ug (20,000 cpm per tube), shows better than two times greater sensitivity when compared to the $^3$H tracer.

Samples from twenty-four patients presently receiving cyclosporin as an immunosuppressive were measured for cyclosporin levels using the above radioimmunoassay with $^3$H-cyclosporin and $^{125}$I-cyclosporin as the tracers. The data presented in Table 1 shows good agreement in the values of cyclosporin levels generated by the use of the two tracers. Excluding patient #1, where the sample was badly hemolyzed thereby causing difficulties in counting the tritium based sample due to color quenching, the values presented in Table 1 give a regression coefficient of 0.94. This indicates that the two tracers provide nearly equivalent data.

TABLE 1

COMPARISON OF PATIENT CYCLOSPORIN VALUES USING $^3$H—CYCLOSPORIN OR $^{125}$I—CYCLOSPORIN AS TRACERS*

| PATIENT NUMBER | $^3$H—CYCLOSPORIN | $^{125}$I—CYCLOSPORIN |
|---|---|---|
| 1 | 365 | 220 |
| 2 | 70 | 50 |
| 3 | 265 | 275 |
| 4 | 90 | 105 |
| 5 | 160 | 165 |
| 6 | 135 | 135 |
| 7 | 160 | 170 |
| 8 | 90 | 120 |
| 9 | 50 | 75 |
| 10 | 50 | 65 |
| 11 | 45 | 70 |
| 12 | 105 | 155 |
| 13 | 50 | 95 |
| 14 | 140 | 220 |
| 15 | 55 | 80 |
| 16 | 100 | 150 |
| 17 | 75 | 115 |
| 18 | 270 | 255 |
| 19 | 140 | 185 |
| 20 | 130 | 160 |
| 21 | 90 | 130 |
| 22 | 200 | 240 |
| 23 | 100 | 145 |
| 24 | 75 | 130 |

*Values for cyclosporin are expressed in ng per ml

Using a gamma labeled cyclosporin tracer has several other advantages in addition to increased sensitivity. These include easy sample preparation, easy and fast sample counting, less background noise, reduced cost for the operator due to not having to use scintillation liquids and the associated problems of quenching (chemical, color and dilution), and possible phase separation. The iodinated cyclosporin tracer has a nonspecific binding of approximately 5–8%, quite comparable to results obtained using $^3$H-cyclosporin. With both tracers, the maximum binding reaches greater than 85%, indicating little breakdown of material. In addition, there appears to be little if any decrease in the ability of $^{125}$I-cyclosporin to be bound by antibody after six months of storage at −20 degrees C.

As an alternative embodiment, cyclosporin A was labeled with fluorescein isothiocyanate. Cyclosporin A was reacted with fluorescein isothiocyanate in 50% ethanol/50% sodium bicacbonate buffer (pH 8.5) for one hour at ambient temperature. The solution was acidified by addition of trifluoroacetic acid to pH 3.0. The fluorescein isothiocyanate labeled cyclosporin was purified by HPLC according to the foregoing procedures. The purified tracer had a specific activity equivalent to 1:1 molar ratio of fluorescein isothiocyanate to cyclosporin as determined by difference spectroscopy.

The purified tracer was assayed according to the foregoing procedures except that the detection signal was measured by fluorescent polarization. The results showed supression of the tracer by the addition of unlabeled cyclosporin (initial binding: 60%; competitive binding: 20%).

The invention may be embodied in other specific forms than those set forth in this specification without departing from the spirit or essential characteristics of the invention. Present embodiments, therefore, are to be considered in all respects as illustrative and not restrictive, the scope of the invention being indicated by the appended claims rather than by the foregoing descriptions, and all changes which come within the meaning and equivalency of the claims are therefore intended to be embraced therein.

We claim:

1. A method of immunoassay useful for measuring the concentration of cyclosporin analytes in sample fluids comprising:

competitively reacting labeled cyclosporin and a cyclosporin analyte with an antibody specific to the cyclosporin analyte and the labeled cyclosporin, the quantity and specific activity of the labeled cyclosporin and the quantity and reactivity of the antibody being sufficient to give a measurable detection signal representative of the ratio of antibody bound labeled cyclosporin to unbound labeled cyclosporin wherein the labeled cyclosporin is labeled cyclosporin A, labeled cyclosporin B, labeled cyclosporin C or labeled cyclosporin D and the labeled cyclosporin is labeled with a radioiodine label or a fluorescent label.

2. The method of claim 1 wherein the labeled cyclosporin is radioiodine labeled cyclosporin A or fluorescent labeled cyclosporin A.

3. The method of claim 1 wherein the labeled cyclosporin is radioiodine labeled cyclosporin C or fluorescent labeled cyclosporin C.

4. The method of claim 1 wherein the competitive reaction comprises simultaneous reaction of the labeled cyclosporin and the cyclosporin analyte with the antibody.

5. The method of claim 1 wherein the competitive reaction comprises first reacting the labeled cyclosporin with the antibody, allowing the first reaction to substantially reach equilibrium and form a reaction product containing antibody bound labeled cyclosporin, unbound labeled cyclosporin and free antibody, and second reacting the cyclosporin analyte with the product of the first reaction.

6. The method of claim 1 wherein the competitive reaction comprises first reacting the cyclosporin analyte with the antibody, allowing the first reaction to substantially reach equilibrium and form a reaction product containing antibody bound cyclosporin analyte, unbound cyclosporin analyte and free antibody, and second reacting the labeled cyclosporin with the product of the first reaction.

7. The method of claim 1 wherein the antibody is bound or attached to a solid support.

8. The method of claim 1 wherein the antibody bound labeled cyclosporin is substantially precipitated by reaction with a second antibody specific to the antibody of the antibody bound labeled cyclosporin.

9. The method of claim 1 wherein the radioiodine label is $^{125}$I or $^{131}$I.

10. The method of claim 1 wherein the fluorescent label is fluorescein isothiocyanate.

11. As an article of manufacture, an immunoassay kit useful for measuring the concentration of cyclosporin analytes in sample fluids comprising:

at least one container with labeled cyclosporin, wherein the labeled cyclosporin is labeled cyclosporin A, labeled cyclosporin B, labeled cyclosporin C or labeled cyclosporin D and the labeled cyclosporin is labeled with a radioiodine label or a fluorescent label; and at least one container with an antibody specific to the labeled cyclosporin.

12. The immunoassay kit of claim 11 wherein the labeled cyclosporin is labeled cyclosporin A.

* * * * *

UNITED STATES PATENT AND TRADEMARK OFFICE
CERTIFICATE OF CORRECTION

PATENT NO. : 4,727,035

DATED : February 23, 1988

INVENTOR(S) : Walter C. Mahoney
John W. Orf

It is certified that error appears in the above-identified patent and that said Letters Patent is hereby corrected as shown below:

On the Cover Sheet, in the Inventor Field, add:

-- John W. Orf, 4849 Greenwich Way North, Oakdale, Minnesota 55109 --

On the Cover Sheet, in the Assignee Field, add:

-- INCSTAR Corporation
Stillwater, Minnesota --

In Column 5, Line 8, delete "bicacbonate" and add:

-- bicarbonate --

On the Title Page, Item [19], "Mahoney" should read -- Mahoney et al. --.

Signed and Sealed this

Fifth Day of December, 1989

Attest:

JEFFREY M. SAMUELS

Attesting Officer  Acting Commissioner of Patents and Trademarks

Disclaimer 4,727,035.—*Walter C. Mahoney*, Woodbury, Minn. IMMUNOASSAY FOR CYCLOSPORIN. Patent dated Feb. 23, 1988. Disclaimer filed June 28, 1990, by the assignee, Sandoz Ltd.

Hereby enters this disclaimer to claims 1-12 of said patent.
[ *Official Gazette Nov. 20, 1990* ]